United States Patent

Bland et al.

[11] Patent Number: 5,965,188
[45] Date of Patent: *Oct. 12, 1999

[54] ANTI-BACTERIAL AMINE DERIVATIVES

[75] Inventors: Bobby J. Bland, Buford; Kurt E. Richardson, Hoschton, both of Ga.

[73] Assignee: Anitox Corporation, Buford, Ga.

[*] Notice: This patent issued on a continued prosecution application filed under 37 CFR 1.53(d), and is subject to the twenty year patent term provisions of 35 U.S.C. 154(a)(2).

[21] Appl. No.: 08/690,109

[22] Filed: Jul. 31, 1996

[51] Int. Cl.$^6$ ........................................................ A23L 3/34
[52] U.S. Cl. ........................ 426/532; 426/321; 426/335; 426/531; 426/656
[58] Field of Search ...................................... 426/532, 656, 426/321, 331, 335, 531, 657

[56] References Cited

U.S. PATENT DOCUMENTS

| | | |
|---|---|---|
| 4,003,865 | 1/1977 | Nowak et al. . |
| 4,534,782 | 8/1985 | Rusznak et al. . |
| 4,587,268 | 5/1986 | Pfirrmann . |
| 4,882,149 | 11/1989 | Spector . |
| 5,043,176 | 8/1991 | Bycroft et al. . |
| 5,210,083 | 5/1993 | Pfirrmann . |
| 5,268,178 | 12/1993 | Calhun et al. . |
| 5,366,989 | 11/1994 | Imaizumi et al. . |

OTHER PUBLICATIONS

Barnes, et al., "The Mechanism of Action of Hexahyrdo–1,3,5–triethyl–s–triazine," *Journal of Industrial Microbiology*, 1 (1986) 105–112.

French et al, "The Reactions of Formaldehyde with Amino Acids and Proteins," *Advances in Protein Chemistry*, vol. II, 1945, 277–335.

Holtzman et al, "Evaluation of Action of a Formaldehyde Condensate Germicide," Department of Biology, Wayne State University, Detroit, Michigan 48202, Chap. 70, pp. 753–758.

Hughey et al, "Antimicrobial Activity of Lysozyme Against Bacteria Involved in Food Spoilage and Food–Borne Disease," *Applied and Environmental Microbiology*, Sep. 1987, pp. 2165–2170.

Pellegrino et al, "Evaluation of the Stable Reaction Products of Histidine with Formaldehyde or with other Carbonyl Compounds in Dairy Products," *Z Lebensm Unters Forsch*, (1996) 202: 66–71.

Sondossi et al, "Factors Involved in Bactericidal Activities of Formaldehyde Condensate/Isothiazolone Mixtures," *Int'l Biodeterioration & Biodegradation*, 32 (1993) 243–261.

Sondossi et al, "Induction and Selection of Formaldehyde–based Resistance in *Pseudomonas aeruginosa*," *Journal of Industrial Microbiology*, 9 (1986) 97–103.

Sondossi et al, "The Effect of Fifteen Biocides on Formaldehyde–resistant Strains of *Pseudomonas aeruginosa*," *Journal of Industrial Microbiology*, 1 (1986) 87–96.

Walker, "Reactions with Amines, Amides and Nitriles," *Formaldehyde*, Reinhold Publishing Corp., pp. 399–404.

"Disinfectants and Antiseptics," *Encyclopedia of Chemical Technology*, 4th Ed., vol. 8, pp. 253–254, 268–269.

Masuya et al. HCA ACS 111:39851, Abstracting EP 271829 Jun. 1988.

Mitsevich et al, HCA ACS 91:69182, Abstracting Byull. Eksp. Biol. Med., 87(5), 466–8, 1979.

Gidley et al., HCA ACS 95:55499, Abstracting FEBS Lett., 127(2), 225–7, 1981.

*Primary Examiner*—Leslie Wong
*Attorney, Agent, or Firm*—Oblon, Spivak, McClelland, Maier & Neustadt, P.C.

[57] ABSTRACT

An antibacterial composition obtained by reacting formaldehyde and a compound having two NH moieties. The product is used to protect food and other items from contamination by *E. coli* 0157:H7 and other bacteria.

14 Claims, No Drawings

ANTI-BACTERIAL AMINE DERIVATIVES

FIELD OF THE INVENTION

Formaldehyde derivatives of amino compounds which kill bacteria and other pathogenic organisms.

DISCUSSION OF THE BACKGROUND

Hemolytic uremic syndrome (HUS) or "hamburger disease" is a growing problem in the United States. It causes severe stomach cramps, bloody diarrhea and is often fatal in children and the elderly. The disease is caused by a bacteria designated as *Escherichia coli* 0157:H7. Major outbreaks can develop before health authorities have a chance to intervene because symptoms do not appear until two to seven days after eating contaminated food and many people infected with the *E. coli* 0157:H7 initially interpret the symptoms as flu and wait for it to pass. In children this delay often results in a progression into late stage infection, which then develops into HUS in about 20% of such cases. About two percent of those contracting HUS die. A well-publicized incident in 1993 involving one particular restaurant in Kings County, WA resulted in well over 400 adults and children becoming infected after eating beef. Two of the children died, several became very ill and one lapsed into a coma. The disease is not confined to undercooked meat and poultry products. A 1991 outbreak of *E. coli* 0157:H7 in the Fall River, Mass. area caused about 23 people to become severely ill after drinking fresh pressed apple cider but no deaths occurred. Direct infection of tissue can also occur in flesh wounds.

At the present time the U.S. population experiences about 20,000 foodborn cases of *E. coil* 0157:H7 infection each year and that number is growing. The *E. coli* 0157:H7 is an especially virulent bacteria. An individual needs only to be infected with a few of the bacteria to suffer food poisoning symptoms because they can grow in the intestine, eventually causing ulcers in the intestinal lining. The bacteria also produce toxins, related to the highly poisonous Shiga toxin, which then enter the blood stream through the intestinal ulcers. The bacterial toxins travel to the kidneys, are trapped there and damage the kidneys, causing HUS. People with HUS have no kidney function and must undergo dialysis for the remainder of their lives or have a kidney transplant.

A number of different antibiotic compounds are known which can eliminate bacterial contamination in food, can disinfect pharmaceuticals and medical equipment, and cure systemic or topical bacterial infections in animals and plants. However, since a low infectious dose is sufficient to cause illness from highly virulent bacteria, merely sterilizing an item once does not make it completely safe because food and other items can easily become recontaminated sometime after the initial sterilization treatment. Chlorine dioxide has recently been approved by the U.S. Food and Drug Administration as a dip for killing *E. coli* and Salmonella on beef. However, its anti-bacterial activity disappears after a short time due to chemical reactions between chlorine dioxide and the organic compounds in the beef so it cannot offer long-term protection against recontamination. The present invention offers a way to kill highly virulent bacteria and to protect the treated item from future bacterial contamination. It also provides systemic and topical treatments for bacterial infection.

SUMMARY OF THE INVENTION

One object of the invention is to provide an antibacterial composition comprising:

a reaction product of (a) formaldehyde and (b) a compound of formula (I) having two NH groups:

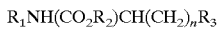

$R_1NH(CO_2R_2)CH(CH_2)_nR_3$ wherein $R_1$ is a $C_{1-10}$ alkyl, $C_{1-10}$ alkenyl, $C_{1-10}$ alkynyl, aryl, 5- or 6-membered heterocyclic, or $R_4CO$— group; $R_4$ is a $C_{1-10}$ alkyl, $C_{1-10}$ alkenyl, $C_{1-10}$ alkynyl, aryl, $C_{1-10}$ alkoxyl, $C_{1-10}$ alkylamino, $C_{1-10}$ dialkylamino or $C_{1-10}$ thioalkyl group;

$R_2$ is H, $C_{1-10}$ alkyl, $C_{1-10}$ alkenyl, $C_{1-10}$ alkynyl, aryl, 5- or 6-membered heterocyclic, $C_{1-10}$ alkoxyl, $C_{1-10}$ alkylamino, $C_{1-10}$ dialkylamino or $C_{1-10}$ thioalkyl group; and $R_3$ is $R_5NH$—, $R_5NHCO$—, $R_5CONH$—, —$NC(=NR_5)$ $NHR_5$, —$NC(=NH)NR_5R_5$ or a heterocyclic radical containing an NH moiety, wherein $R_5$ is independently a $C_{1-10}$ alkyl, $C_{1-10}$ alkenyl, $C_{1-10}$ alkynyl, aryl, 5-membered or 6-membered heterocyclic group and n is an integer between 0 and 6.

Another object of this invention is to provide a human or animal foodstuff that is free of contamination by *E. coli* 0157:H7 and is resistant to subsequent contamination by the bacteria, which contains a reaction product of formaldehyde and a compound of formula (I).

Another object is to provide a method for disinfecting or protecting an item from bacterial contamination comprising: treating an item subject to bacterial contamination with an effective amount of a reaction product of (a) formaldehyde and (b) a compound of formula (I).

Another object is to provide an antibacterial composition comprising: 1–50 wt. % of a reaction product of (1) lysine, arginine, histidine, glutamine, threonine or asparagine and (2) formaldehyde; or a salt thereof, and a carrier.

Another object is to provide an antibacterial compound of formula $H_2N(CO_2H)CH(CH_2)_4NHCH_2NH(CO_2H)CH(CH_2)_4NH_2$ or a salt thereof.

DETAILED DESCRIPTION OF THE PREFERRED EMBODIMENTS

The amine-formaldehyde adducts of this invention are useful as (1) chemical preservatives for human and animal foods to prevent microbial deterioration of foodstuffs and prolong shelflife, (2) disinfectants to reduce, eliminate or prevent bacterial contamination of foods and other items such as those made of cloth, plastic and metal and (3) treatment for systemic or topical bacterial infections in plants and animals.

The antimicrobial compounds of this invention are produced by exposing a compound of formula (I) above, in solution or in the solid state, to formaldehyde thereby forming products which kill microorganisms, including bacteria in the genera Escherichia, Salmonella, Listeria, Clostridium, Bacillus, Staphylococcus, Campylobacter and Yersinia. They are particularly useful for controlling organisms of concern in food safety, such as *E. coli* 0157:H7, *Listeria monocytogenes, Clostridium botulinum, Clostridium hermosaccharolyticum, Bacillus stearothermophilus, Clostridium tyrobutyricum, Bacillus cereus, Clostridium perfringens, Staphylococcus aureus, Campylobacter jejuni, Salmonella typhimurium* and *Yersinia enterocolitica*.

Microorganisms of concern in crop protection which can be controlled with the present invention include species of genera Agrobacterium, Erwinia, Pseudomonas, Xanthomonas, and Bacillus.

Infections in animals which can be treated with the product of the invention include species of genera Streptococcus, Staphylococcus, Corynebacterium, Listeria, Erysipelothrix, Bacillus, Clostridium, Eschericheria, Salmonella, Pasteurella, Brucella, Hemophilus, Moraxella, Mycobacterium, Actinomyus, Actinobacillus, Nocardia, Dermatophilus, Fusobacterium, Campylobacter, and Leptospira.

In this disclosure resistance to contamination means that a challenge with 1000 cfu of *E. coli* 0157:H7 per gram of foodstuff results in 1 cfu or less per 25 grams of foodstuff after 24 hours incubation at 25° C.

The compounds of the present invention maintain their biological activity for extended periods in aqueous solution and so are thought not to be formaldehyde releasers however, the mode of action is not known at this time. The chemical reaction forming the product can be characterized as a condensation reaction.

The compounds of formula (I) can be reacted as the free amine, or as the salt of an organic or inorganic acid. The hydrochloride salt tends to enhance water solubility and is the preferred salt. Other salts which can be used are acetate, formate and sulfate. When the reaction with formaldehyde is conducted in solution, the preferred solvent is water or a mixture of water and a Coo alcohol. Other organic solvents which may be used include halogenated hydrocarbons, ethylacetate, acetonitrile and dimethylformamide. When reacting the solid compound of formula (I), the free base is preferred.

The formaldehyde is conveniently provided by passing air or nitrogen (300 to 500 cc/min) through a solution of 37% aqueous formaldehyde (formalin) or heating solid paraformaldehyde under a stream of air or nitrogen to form gaseous formaldehyde and entraining the gas into a solution of compound (I) or over the powdered solid of compound (I) while agitating the powder. The reaction generally requires from 1 to 15 molar equivalents of formaldehyde.

The product is isolated by evaporating the solvent under reduced pressure and purifying the residue by column chromatography over Sephadex, ion exchange resins, silica gel or reversed phase (hydrophobic) resins, by well known procedures using solvents such as water, $C_{1-4}$ alcohols, acetonitrile, ethyl acetate, $C_{1-10}$ hydrocarbons and mixtures thereof.

Animal food products which can be made resistant to contamination using the amine derivatives include but are not limited to beef, swine, poultry, sheep, fish and other seafood. In general, the antibacterial composition is dusted on the surface of the food product or the product is dipped into an aqueous solution of the antibacterial of 0.1 to 1.0 wt % concentration. If the animal product has been ground, such as hamburger or sausage, the antibacterial composition should be added in an amount of 0.1 to 1.0 wt % either as a solid or in 0.1 to 1.0 wt % solution.

Animal feeds can be disinfected and rendered resistant to contamination. Examples include but are not limited to broiler starter feed and broiler grower feed.

Specific items which can be protected from bacterial contamination include water, milk, cheese, chicken carcasses, all types of fish meal, egg whites for mayonnaise, ground beef, processed meats, bananas, tomatoes, other fruits and vegetables, diaper rash products, powdered or liquid baby formula, products for prevention or treatment of feminine yeast infections, flowers and soap.

Specific uses for the disinfectant solution include cleaners for hospitals, nursing homes, daycare centers and doctor's offices, salves for sores, coatings for gloves and clothing in operating rooms, sprays to kill bacteria in open areas during surgery, sprays to kill bacteria in AIDS care facilities, medications, paper tissues, wet wipes, air duct systems, bandages litter boxes, crop dusting compositions, cleaning of trucks or containers which carry liquid or bulk foods, packaging for foods, air sprays similar to Lysol®, cleaners for showers and toilets, teat dips for dairy cows, wash for deer to keep the meat fresh while going to a freezer or processing house, floor coverings in animal pens, swabs to cleanse mouth before paramedics give mouth to mouth resuscitation, cleaners for medical or dental instruments, preservatives for human foods, preservatives for dog foods, preservative in canned foods, toothpaste additive and mouthwash additive.

Preferred egg-containing products are processed eggs, egg nog, mayonnaise, salad dressings, noodles, and bakery goods. Preferred milk-containing products are powdered milk, infant formula, ice cream, yogurt, milk chocolates, creamers and cheeses.

In formula (I) above, the term aryl means substituted or unsubstituted phenyl and substituted or unsubstituted naphthyl. Heterocyclic groups containing an NH moiety include pyrrolyl, imidazolyl, pyrazolyl, isoindolyl, indolyl, pyrrolidinyl, imidazolinyl and indolinyl. A preferred group is the 5-imidazolyl group of histidine. The term 5- or 6-membered heterocyclic group means unsubstituted or substituted thiophenyl, furyl, pyrrolyl, imidazolyl, pyridyl, isoxazolyl, imidazolidinyl, piperidyl, piperazinyl and morpholinyl groups. The optional substituents on the aryl groups, heterocyclic groups containing an NH moiety, 5- and 6-membered heterocyclic groups are $C_{1-10}$ alkyl, $C_{1-10}$ alkenyl, $C_{1-10}$ alkoxyl, fluoro, chloro, bromo, iodo, $C_{1-10}$ mono- or di-alkylamino, $C_{1-10}$ alkoxyl and cyano.

The present invention is illustrated by the following non-limiting examples.

EXAMPLE 1 d,l-Lysine (2,6-diaminohexanoic acid) was finely ground and dried in vacuo. The dried powder (100 g) was transferred to a one liter round bottom flask. Formaldehyde vapors were generated by aeration (500 ml/min) of formalin (37% formaldehyde in water) and passed over the surface of the powder for 96 hours. The product was dried in vacuo and purified by column chomotography over Sephadex G-10 (600 ml), and eluted with distilled water. Fractions of column effluent were collected on a timed basis and fractions containing the product were identified using the Bradford method for protein determination. Fractions containing the product were combined and freeze dried to a dry powder. The yield was 40% and in the Bradford method, a blue dye is bound to the aromatic groups of specific amino acids in proteins. The concentration of protein is determined by comparison with a standard curve. The dye will bind to other groups of amino acids but is less sensitive (specific).

EXAMPLE 2

The amino acids listed below (2 g) were dissolved in 200 ml of deionized water in individual 500 ml Erlenmeyer flasks. Formaldehyde was added to each aqueous solution by aeration (500 ml/min) of a 37% formaldehyde solution for six hours. The solution was frozen and dehydrated by freeze drying. The residue was transferred to an aluminum pan and any residual formaldehyde evaporated by drying at 40° C. for 24 hours. The adducts were then dried at 60° C. for 48 hours. Stock solutions of adducts were obtained by dissolving 100 mg of the adduct in 10 ml of 98% ethanol (10 mg/ml). The stock dilution was diluted in water for antimicrobial testing.

Antimicrobial Testing of Adducts

Cultures of *Salmonella typhimurium* and *Escherichia coli* (0157:H7) were transferred to veal infusion broth and incubated at 37° C. for 24 hours. The number of bacterial cells/ml was determined by serial dilution and selective agar plating. The concentration of bacteria/ml were diluted to $10^7$ with veal infusion broth. An aliquot of the adduct solution was added to test tubes of veal infusion broth containing Salmonella or E. coli to achieve a final concentration of 1 mg/ml of adduct. Cultures were incubated at 50° C. for 1 and 24 hours. Free lysine and the lysine adduct were used as negative and positive controls. At 1 and 24 hours after treatment, 100 μl of the veal infusion broth was plated on selective agar plates. The plates were incubated at 37° C. prior to enumeration of the bacteria.

| Treatment | E. coli | Salmonella |
| --- | --- | --- |
| Control | $7.13 \times 10^6$ | $>1.31 \times 10^7$ |
| Lysine | $6.17 \times 10^6$ | $>1.31 \times 10^7$ |
| Lysine adduct | 0 | $1.10 \times 10^6$ |
| Arginine adduct | 0 | $1.31 \times 10^7$ |
| Histidine adduct | 0 | $9.73 \times 10^5$ |
| Asparagine adduct | $2.76 \times 10^3$ | $9.57 \times 10^5$ |

EXAMPLE 3

Protocol for Testing Anti-bacterial Compounds for Preservation of Hamburger Meat 1. 1 kg of commercially prepared hamburger meat is thoroughly mixed and divided into two 500 g subsamples.

2. An aliquot of veal infusion broth containing *Escherichia coli* 0157:H7 is added to each 500 g subsample to obtain a final concentration of 100 colony forming units/g.

3. 50 of an aqueous solution of anti-bacterial compound obtained according to Example 2 (10 wt % solution) is added to one subsample and thoroughly mixed with the hamburger meat.

4. 50 g of deionized water (control treatment) is added to the second subsample and thoroughly mixed with the meat.

5. 25 g of the treated meat is placed in a sterile petri plate and incubated at 7–8° C. for 5 days. There are 10 replicate samples per treatment.

6. After 5 days, one replicate of each treatment is removed from the petri plate and transferred to a 500 ml bottle containing 225 ml of buffered phosphate solution.

7. The solution is agitated on a wrist action shaker for 30 min., serially diluted with sterile buffered phosphate solution and plated on selective agar.

8. Inoculated plates are incubated at 35° C. for 24 hr. prior to enumeration of *E. coli*, total bacteria and enterobacteriaceae.

9. Steps 6 through 8 are repeated on days 6, 7, 8, 9, 10, 12, 14, 16 and 18.

EXAMPLE 4

Enumeration of Coliform Bacteria in Feed and Feedstuffs

Bacteria are suspended in a phosphate-buffered solution by mechanical agitation. Supernatant is plated on selective media and incubated 18–24 hours prior to enumeration.

Reagents: TX-100 Stock Solution: Pipet 20.0 g of Triton X-100 into a 500 ml nalgene reagent bottle. Add 400 ml of deionized water and stir. Store in the refrigerator. The solution can be stored for up for up to 4 weeks.

Butterfield's Phosphate/TX-buffered diluent (BX): Dissolve 510 g of potassium phosphate ($KH_2PO_4$) in 7500 ml of deionized water in a 15 L carboy. Add 2850 ml of 1N sodium hydroxide (NaOH) to adjust pH to 7.2. Add 4650 ml of deionized water to adjust volume to 15 liters. Add 127.5 ml of sodium chloride (NaCl). Pipet in 15 ml TX-100 stock solution. Dispense into 2 L reagent bottles. Autoclave for 45 minutes @ 121° C. (Note: Just set cap on bottle during autoclaving.) When reagent has cooled to room temperature, aseptically attach the sterile Brinkmann Dispensette and check calibration.

MacConkey Agar Plates: Add 50 g of MacConkey agar base to 1 L of deionized water to the agarmatic vessel. (Up to a maximum capacity of 3 L/run.) Sterilize for 15 minutes. When cycle is complete, connect sterile dispensing assembly. Prepare and operate the Pourmatic dispensing 14 ml/plate. Carefully remove each stack from the carousel to the level counter to the left of agarmatic, stacking the plates on transfer trays to solidify. Encode plates with quality control batch information promptly.

PROCEDURE: Use a sample splitter to obtain approximately 10 grams of the feedstuff to be tested. The subsample should be representative of the lot of feedstuff being tested. In most instances, failure to obtain a representative subsample for testing can account for up to 95% of the error in the analysis. Weigh 10.00+/-0.01 g of the subsample in the sample processing bottle. Dispense 90 ml of BX solution into the sample bottle. Cap tightly and shake vigorously for 30 minutes on a wrist-action shaker. Label spiral-quality plates with the sample number, and spread plates with the sample number and replicate designations "A", "B" and "C". Turn on the Electrapette console and select the bacteria plating program. Using a sterile 1000 ul tip, transfer 100 ul of sample supernatant to each of three replicate plates. (If sample clogs the tip, use a sterile pasteur pipet.) Spread sample using a flamed (95% ethanol) glass rod. Set up the sterile filtration apparatus with labelled sample cups, replace filtering block and remove drip shield. Lightly agitate sample before pipetting. Using a sterile, large-volume pipet and the Pipet-aid, transfer approximately 4 mls of the sample supernatant through the filter and into the cup. After filtering, replace the drip shield before removing the filtering block to prevent cross-contamination. Cover samples with aluminum foil and carefully transfer the rack from the hood to the spiral plater. Plate sample using the spiral plater. Carefully invert all plates and place in a 37° C. incubator with the A replicates on the top shelf, B replicates on the middle shelf and the C replicates on the lower shelf. After 24 hours of incubation, colony forming units can be enumerated. Coliform bacteria colonies are pink to red in color with or without a zone of precipitated bile.

REFERENCES: Bacteriological Analytical Manual (1984). 6th Edition, A.O.A.C., Arlington, Va. Difco Manual (1985). 10th Edition. Detroit, Mich.

EXAMPLE 5

Formation of Formaldehyde:Lysine Adduct

Feed grade lysine monohydrochloride (98.2% purity) was obtained as a powder from a commercial mill and mixed with a 37% formaldehyde solution by spray application while mixing the powder. The molar ratios of formaldehyde to lysine are presented in the following table.

| SAMPLE | FORMALDEHYDE MOLES | LYSINE MOLES | RATIO |
| --- | --- | --- | --- |
| 1 | 0 | 7.46 | — |
| 2 | 6.7 | 7.46 | 1:1.2 |
| 3 | 13.3 | 7.46 | 1.78:1 |
| 4 | 26.7 | 7.46 | 3.56:1 |

-continued

| SAMPLE | FORMALDEHYDE MOLES | LYSINE MOLES | RATIO |
|---|---|---|---|
| 5 | 53.5 | 7.46 | 7.13:1 |
| 6 | 106.7 | 7.46 | 14.3:1 |

After application of the formaldehyde, the products were transferred to open containers and stored for 3 days to allow formaldehyde vapors to dissipate.

Treatment of Feed

Poultry starter mash was contaminated with a liquid culture (2 ml/kg mash) of Salmonella ($10^8$ cfu/ml). The lysine adducts were mixed with the mash at 0.5:100, 1:100, or 2:100 weight ratio. After twenty-four hours, the feed was assayed for Salmonella.

| | # SALMONELLA COLONIES/G Ratio of Adduct/Feed | | |
|---|---|---|---|
| SAMPLE | 0.5:100 | 1:100 | 2:100 |
| 1 (Control) | — 2,280,000 | 2,280,000 | 2,280,000 |
| 2 | — | 281,000 | 281,000 |
| 3 | — | 98,200 | 38,300 |
| 4 | — | 209,000 | 951,000 |
| 5 | 70,200 | 22,200 | 4,990 |
| 6 | 82,900 | 27,600 | 3,890 |

This data demonstrates there is bacteriocidal activity.

Formation of Formaldehyde:Lysine Adduct

Feed grade lysine monohydrochloride (98.2% purity) was obtained from a commercial mill and ground to a fine powder. Formaldehyde (37% solution) was added to the powdered lysine while mixing by spray application. After the lysine was saturated with formaldehyde, unbound formaldehyde was removed from the lysine by drying at 35–40% under partial vacuum for five days. Residual formaldehyde was determined (0.203%) by distillation and colormetric derivitization.

Treatment of Feed

Poultry feed was sterilized by autoclaving for one hour on two consecutive days. The sterile feed was contaminated with a liquid broth culture (2 ml/kg feed) of Salmonella ($10^8$ cfu/ml) and the bacterial population allowed to stabilize for 24 hours. The lysine adduct was mixed with the contaminated feed at 0, 2, 8, 16, and 32 kg/ton treatment levels. Twenty four hours after treatment, the feed was assayed for Salmonella.

| Treatment | # Salmonella/g |
|---|---|
| Control | 175,000 |
| 2 kg/ton | 14,700 |
| 4 kg/ton | 8,280 |
| 8 kg/ton | 3,860 |
| 16 kg/ton | 333 |
| 32 kg/ton | 0 |

EXAMPLE 9

Formation of Formaldehyde:lysine Adduct

Feed grade lysine monohydrochloride (98.2% purity) was obtained from a commercial mill and ground to a fine powder. Formalin (37% formaldehyde solution) was added by spray application to the powdered lysine while mixing. After the lysine was saturated with formaldehyde, "unbound" formaldehyde was removed from the lysine by drying at 35–40° C. under partial vacuum for five days. Residual formaldehyde was determined (2.03%) by distillation and colormetric derivitization.

Treatment of Feed

Poultry feed was purchased from a commercial mill and sterilized by autoclaving for one hour on two consecutive days. The sterile feed was contaminated with a liquid broth culture of E. coli (2 ml/kg feed; $10^5$ cfu/ml) and the bacterial population allowed to stabilize for 24 hours. The lysine adduct was mixed with the contaminated feed at 0, 2, 4, 8, 16, and 32 kg/ton treatment levels. Twenty four hours after treatment, the feed was assayed for E. coli.

Results

| Treatment | # E. coli/g |
|---|---|
| Control | 133 |
| Lysine adduct - 2 kg/ton | 33 |
| Lysine adduct - 4 kg/ton | 33 |
| Lysine adduct - 8 kg/ton | 0 |

Obviously, numerous modifications and variations are possible in view of the above teachings, and within the scope of the appended claims, the present invention can be practiced otherwise than as specifically described herein.

We claim:

1. A foodstuff which is free of contamination by E. coli 0157:H7 comprising: a reaction product of (a) formaldehyde and (b) lysine;

or a salt of said reaction product.

2. The foodstuff of claim 1 wherein a challenge with 1000 cfu of E. coli 0157:H7 per gram of foodstuff results in 1 cfu or less per 25 grams of foodstuff after 24 hours incubation at 25° C.

3. The foodstuff of claim 1 which contains 0.1–10 wt % of said reaction product, based on the total weight of the foodstuff.

4. The foodstuff of claim 1 which contains a component of animal origin.

5. The foodstuff of claim 4 wherein said component of animal origin is ground beef.

6. A foodstuff containing 0.1–20 wt % of a preservative having the structure $H_2N(CO_2H)CH(CH_2)_4NHCH_2NH(CO_2H)CH(CH_2)_4NH_2$ or a salt thereof.

7. The foodstuff of claim 6 wherein a challenge with 1000 cfu of E. coli 0157:H7 per gram of foodstuff results in 1 cfu or less per 25 grams of foodstuff after 24 hours incubation at 25° C.

8. The foodstuff of claim 7 which contains a component of animal origin.

9. The foodstuff of claim 8 wherein said component of animal origin is ground beef.

10. A method for protecting foodstuff from bacterial contamination comprising: treating a foodstuff subject to bacterial contamination with an effective amount of a reaction product of (a) formaldehyde and (b) lysine:

or a salt of said reaction product.

11. The method of claim 10 wherein said treated foodstuff is resistant to contamination by E. coli 0157:H7 such that challenge with 1000 cfu of E. coli 0157:H7 per gram of foodstuff results in 1 cfu or less per gram of foodstuff after 24 hours incubation at 25° C.

12. The method of claim 11 wherein said foodstuff contains a component of animal origin.

13. The method of claim 10 wherein the foodstuff is treated with 0.1–10 wt. % of said reaction product, based on the total weight of the protected foodstuff.

14. The method of claim 10 wherein said reaction product is $H_2N(CO_2H)CH(CH_2)_4NHCH_2NH(CO_2H)CH(CH_2)_4NH_2$ or a salt thereof.

* * * * *